United States Patent [19]
Sheth et al.

[11] Patent Number: 4,588,589
[45] Date of Patent: May 13, 1986

[54] ANTIDIARRHEAL COMPOSITIONS AND USE THEREOF

[75] Inventors: Bhogilal B. Sheth, Norwalk; Sheri A. Gilbert, Stratford; Jane F. Kinsel, Derby, all of Conn.

[73] Assignee: Richardson-Vicks Inc., Wilton, Conn.

[21] Appl. No.: 541,551

[22] Filed: Oct. 13, 1983

[51] Int. Cl.⁴ .................. A61K 35/78; A61K 31/715; A61K 31/60
[52] U.S. Cl. .................. 424/195.1; 514/57; 514/159
[58] Field of Search ............ 424/195, 195.1; 514/159, 57

[56] References Cited
PUBLICATIONS

Conn, Current Therapy, 1981, Saunders Co., Philadelphia, pp. 421–423.
Handbook of Nonprescription Drugs, 1977, pp. 48 and 222.

Primary Examiner—Jerome D. Goldberg
Assistant Examiner—John W. Rollins
Attorney, Agent, or Firm—George W. Rauchfuss, Jr.; Salvatore R. Conte

[57] ABSTRACT

Antidiarrheal compositions showing enhanced antidiarrheal activity comprise bismuth subsalicylate and a polymeric hydroabsorptive agent selected from psyllium and glucomannan. A patient in need of remedial or preventive treatment of diarrhea symptoms is administered an antidiarrheally effective amount of said antidiarrheal compositions.

20 Claims, 6 Drawing Figures

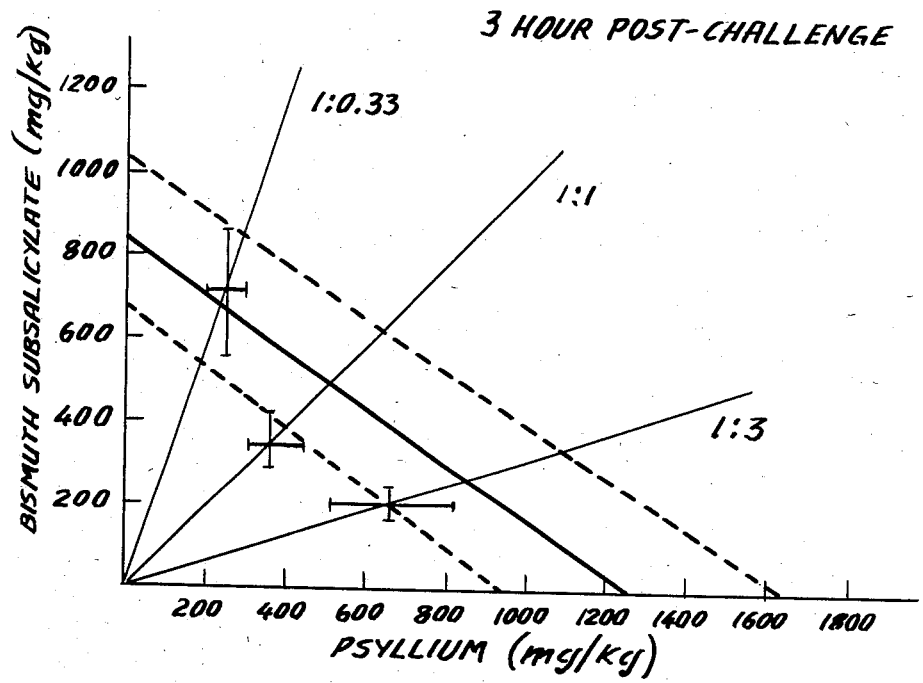
Fig. 3. ISOBOLOGRAMS FOR THE INTERACTION OF BISMUTH SUBSALICYLATE (BSS) AND PSYLLIUM
3 HOUR POST-CHALLENGE
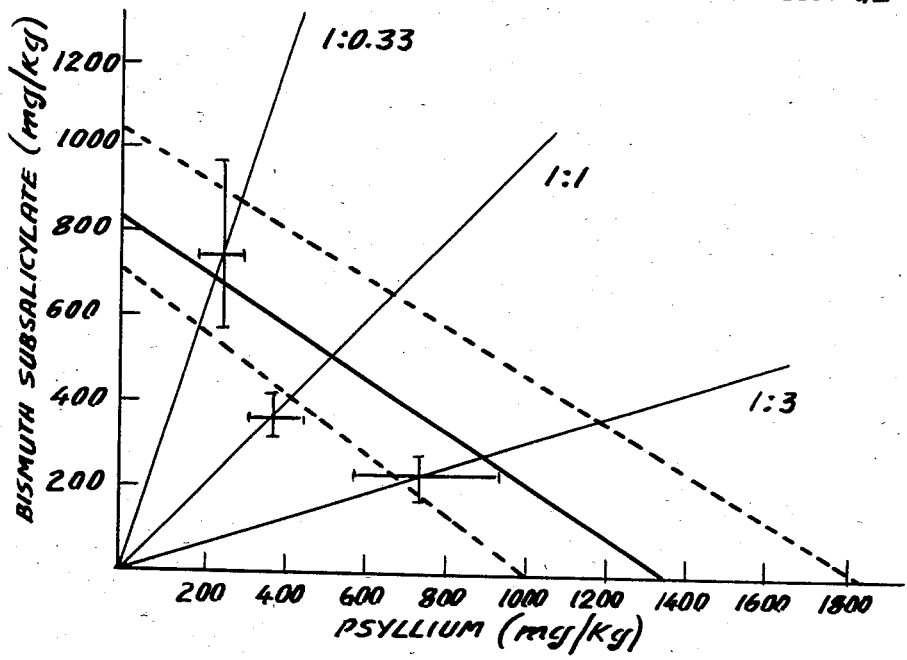
Fig. 4.
4 HOUR POST-CHALLENGE

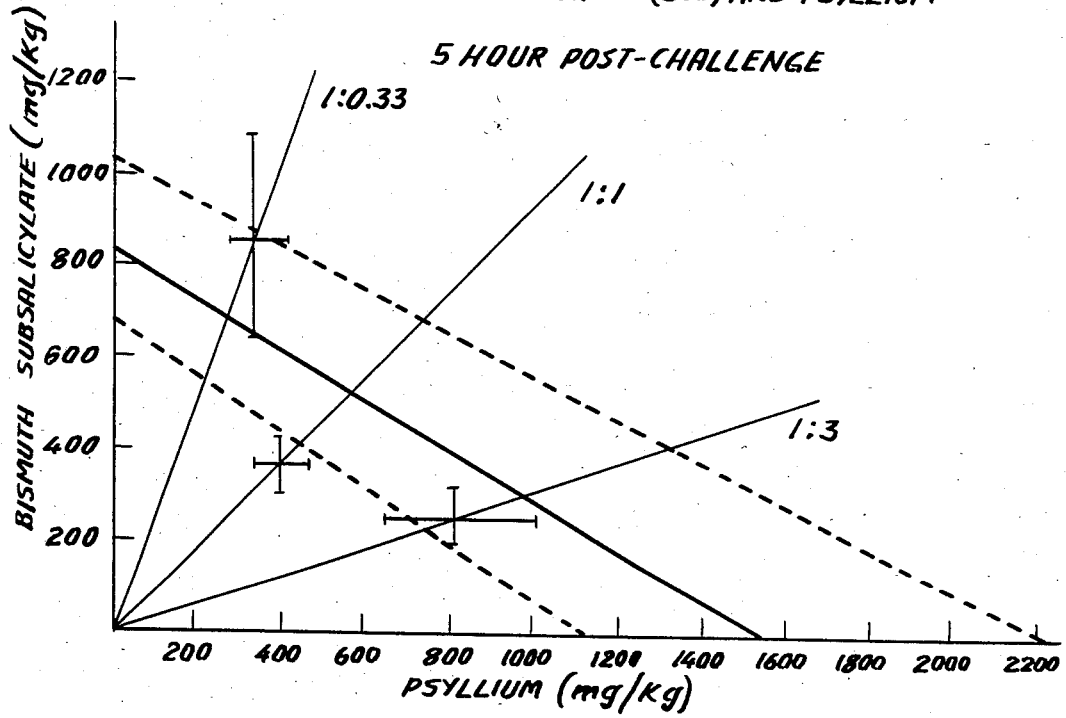
Fig. 5. ISOBOLOGRAMS FOR THE INTERACTION OF BISMUTH SUBSALICYLATE (BSS) AND PSYLLIUM
5 HOUR POST-CHALLENGE
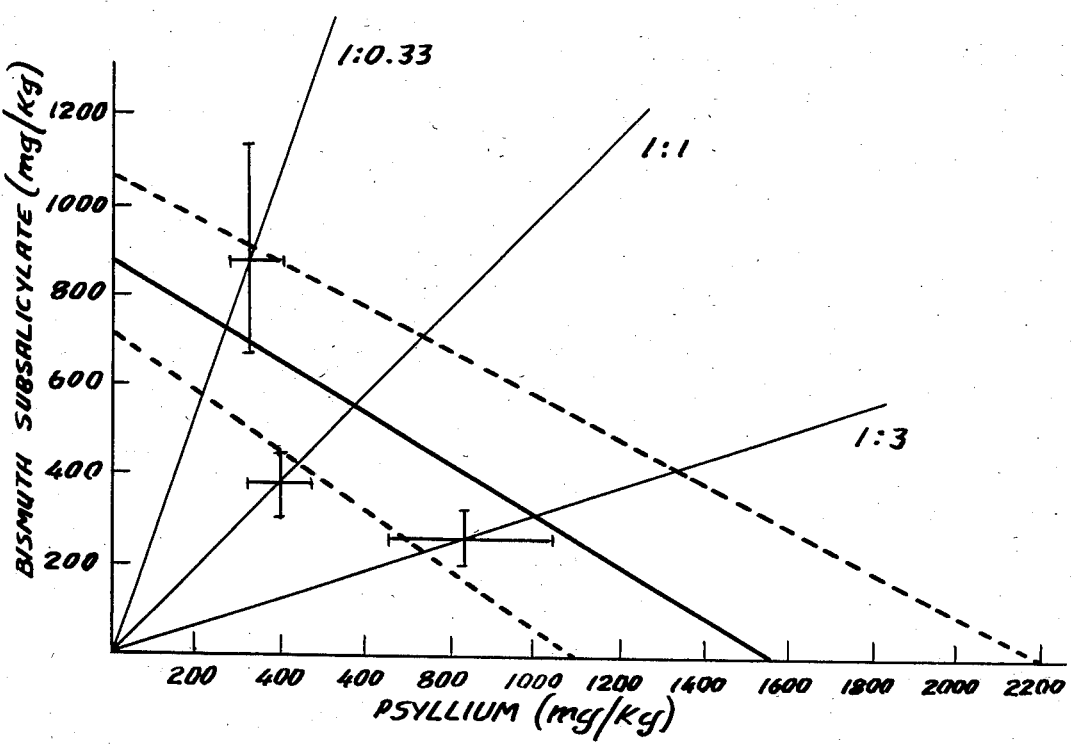
Fig. 6. 6 HOUR POST-CHALLENGE

ANTIDIARRHEAL COMPOSITIONS AND USE THEREOF

FIELD OF THE INVENTION

This invention relates to antidiarrheal compositions of enhanced antidiarrheal activity and to the use thereof to treat a patient in need of preventative or remedial treatment of diarrhea symptoms.

BACKGROUND OF THE INVENTION

Diarrhea can result from a variety of pathophysiological disorders including bacterial and parasitic infections, disease or debilitation of organs such as liver, adrenal and others. It can also occur as a result of other therapy or diet. In all cases, diarrhea is generally a symptom of organic gastrointestinal disorders and not itself a disorder. Chronic diarrhea is generally due to intestinal hypermotility and rapid transport. It may also be due to, or accompanied by hypersecretion of acid gastric juices or decreased reabsorption and may, in some instances, particularly those accompanied by hypersecretion, be associated with emotional tension and psychological conflicts.

Antidiarrheal compounds are, of course, well-known in the medicinal arts and take various forms. In particular there are a variety of products known which act systemically to provide antidiarrheal effects when administered in a manner which will enable the drug to be taken into the system at effective therapeutic levels.

One known antidiarrheal compound is, for example, bismuth subsalicylate which has been shown to be effective in the treatment and prevention of diarrhea symptoms. However, bismuth subsalicylate may be a problem if patients are taking aspirin or taking other salicylate-containing drugs since toxic levels of salicylate may be reached even if the patient follows label directions for each drug. Also, high blood salicylate levels may exert an antiplatelet effect.

It would therefore be highly desirable to be able to potentiate the antidiarrheal activity of bismuth subsalicylate and to provide more effective antidiarrheal activity and to lower the effective dosage levels of bismuth subsalicylate. Also advantageous would be the ability to increase the duration of the antidiarrheal activity thereof.

SUMMARY OF THE INVENTION

Antidiarrheal compositions of enhanced antidiarrheal activity and increased duration of antidiarrheal activity are provided by compositions of bismuth subsalicylate and a polymeric hydroabsorptive agent selected from psyllium and glucomannan. Administration of an antidiarrheally effective amount of said compositions to patients would provide remedial or preventive treatment of diarrhea symptoms.

BRIEF DESCRIPTION OF THE DRAWING

The drawings show graphs (isobolograms) of the interaction of bismuth subsalicylate and psyllium in the castor oil-induced diarrhea test in rats at hours 1, 2, 3, 4, 5, and 6 post-challenge.

DETAILS OF THE INVENTION

Figure 1:
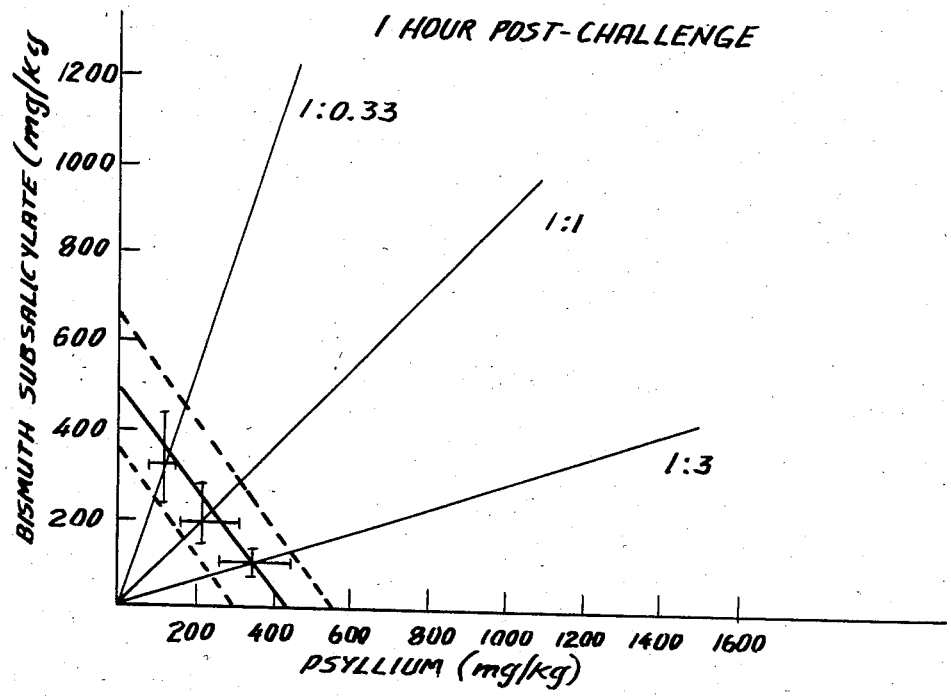
Figure 2:
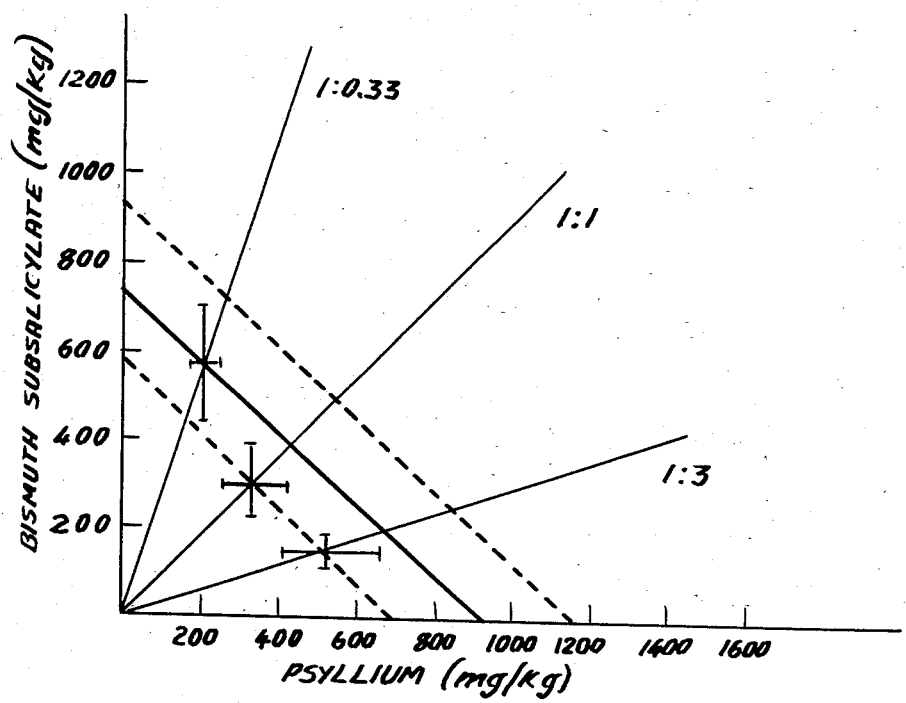

The antidiarrheal activity of bismuth subsalicylate has been found to be potentiated when administered concurrently with a polymeric hydroabsorptive agent selected from psyllium and glucomannan. Especially preferred is psyllium.

Psyllium (plantago seed) useful in the compositions of this invention is described in Pharmacopeia XX, page 634, U.S. Pharmacopeial Convention, Inc. 1980. Glucomannan useful in the compositions of this invention is described in the article titled "Japanese Diet Food" on page 22 of the September 1980 issue of Food Engineering. Glucomannan is a hydrophilic hemicellulose extract from the konjac root and is sold as an appetite curb under the trademark REGAL MANNAN by Regal Vitamin Co., Costa Mesa, Calif.

While it has surprisingly been found that the antidiarrheal activity of bismuth subsalicylate is enhanced by the polymeric hydroabsorptive agents psyllium and glucomannan it has been found that other types of hydroabsorptive agents, for example, hydroabsorptive agents such as the known antidiarrheal compounds malethamer and polycarbophil, do not enhance the antidiarrheal activity of bismuth subsalicylate and in fact antagonize or lower the antidiarrheal activity.

The relative amounts of bismuth subsalicylate and psyllium and glucomman in the compositions of this invention that provide the enhanced antidiarrheal activity is in the range of ratio of bismuth subsalicylate to polymeric hydroabsorptive agent of from about 1:0.5 to about 1:2.9.

The compositions of this invention have been found to exhibit the enhanced antidiarrheal activity for up to six hours after challenge.

The compositions of the present invention can be prepared in forms suitable for administration to humans and animals by compounding an effective single dose amount of the composition of the active ingredients of this invention with known ingredients generally employed in the preparation of therapeutic compositions provided as tablets, capsules, lozenges, chewable lozenges, pills, powder, granules, suspensions, or other similar forms which can be taken orally. In general the composition of the active ingredients of this invention above are indicated for use as pharmacotherapeutic agents in a wide variety of mammalian conditions which require relief of diarrhea symptoms accompanying abnormal action of the gastrointestinal system.

The dosage regimens in carrying out the pharmacotherapeutic methods utilizing the compositions of this invention are those which insure maximum therapeutic response until improvement is obtained and thereafter the minimum effective level which gives relief. Thus, in general, the dosages are those that are therapeutically effective in the treatment of diarrhea. In general, the single oral dose will contain between about 100 mg and 3000 mg (preferably in the range of 300 to 1000 mg) of bismuth subsalicylate and 50 mg to 9000 mg (preferably 150 mg to 3000 mg) psyllium or glucomannan administered concurrently or together as a single formulation. Fractional or multiple doses can of course be given bearing in mind that in selecting the appropriate dosage in any specific case, consideration must be given to the patient's weight, general health, age, and other factors which may influence response to the drug. The drug response on oral administration usually follows within 10 to 30 minutes after administration and is maintained for 1 to 6 hours. The drug is generally given in single doses up to 8 times daily or as required to maintain effective continuous relief of diarrhea symptoms.

Compositions intended for oral use may be prepared according to methods known generally in the art. Such compositions may contain one or more agents selected from the group consisting of sweetening agents, flavoring agents, coloring agents and preserving agents in order to provide a pharmaceutically elegant and palatable preparation. Orally, they may be administered in tablets, lozenges, oily suspensions, dispersible powders or granules, or hard or soft capsules which contain the active ingredients in admixture with non-toxic pharmaceutically acceptable excipients. Excipients which may be, for example, inert diluents, such as calcium carbonate, magnesium carbonate, calcium phosphate, calcium sulphate, lactose, cellulose, microcrystalline cellulose, starch, modified starch, dextrose, sucrose, mannitol, sorbitol; binding agents, for example, polyvinyl pyrrolidone, cellulose ethers such as sodium carboxymethylcellulose, methyl cellulose, hydroxypropyl cellulose, hydroxypropylmethyl cellulose, hydroxy ethyl cellulose and ethyl cellulose, natural gums such as acacia, tragacanth, pectin, guar and karaya, gelatin, alginates, starch, modified starch, polyethylene glycol, microcrystalline cellulose, sugars such as sucrose, sorbitol and glucose, corn syrups, polyvinyl alcohols, polyacrylamides, or polyvinyloxoazolidone; disintegrants, such as, cross linked polyvinyl pyrrolidone, sodium starch glycollate, cross-linked carboxymethyl cellulose, ion exchange resins, starch, modified starches, microcrystalline cellulose, cellulose, cellulose derivatives, alginates, alginic acid or clays; lubricants, glidants and anti-adherants, such as for example, silicone fluids, hydrogenated vegetable oils, light mineral oil, microfine silicas, metallic stearates, stearic acid, polyethylene glycol, talc, corn starch, sodium benzoate, sodium acetate, polyoxyethylene monostearate, magnesium carbonate or magnesium oxide. The tablets may be uncoated or they may be coated by known techniques to make them more effective, to delay disintegration or absorption or to make them more palatable or for other reasons for which orally administered drugs have been previously provided in coated form.

Formulations for oral use may also be presented as hard gelatin capsules wherein the active ingredient is mixed with an inert solid diluent, binding agent, disintegrant, lubricant, glidant or anti-adherent as described hereinbefore for tablets, or as soft gelatin capsules wherein the active ingredient is mixed with an oil medium, for example, arachis oil, liquid paraffin or olive oil.

Oily suspensions may be formulated by suspending the composition of the active ingredients in a vegetable oil, for example, arachis oil, olive oil, sesame oil or coconut oil, or in a mineral oil, such as liquid paraffin. The oil suspensions may contain a thickening agent, for example, beeswax, hard paraffin or cetyl alcohol. Sweetening agents, such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredients in admixture with dispersing, wetting agent or suspending agents. These excipients are suspending agents, for example, sodium carboxymethyl cellulose, hydroxypropyl methylcellulose, sodium alginate, polyvinylpyrrolidine, gum tragacanth and gum acacia; dispersing or wetting agents may be a naturally occurring phosphatide, for example, lecithin; or condensation products or an alkylene oxide with fatty acids, for example, polyoxyethylene stearate; or condensation products of ethylene oxide with long-chain aliphatic alcohols, for example, heptadecaethyleneoxy-cetanol; or condensation products of ethylene oxide with partial esters derived from fatty acids and a hexitol, for example, polyoxyethylene sorbitol monooleate; or condensation products of ethylene oxide with partial esters derived from fatty acids and hexitol anhydrides, for example, polyoxyethylene sorbitan monooleate. They, may also include one or more preservatives, for example, ethyl, or n-propyl, p-hydroxy benzoate, one or more coloring agents, one or more flavoring agents, and one or more sweetening agents, such as sucrose.

Generally, these compositions may be tableted or otherwise formulated for oral use so that for every 100 parts by weight of the composition, there are present between 5 and 95 parts by weight of the active ingredients.

The enhanced antidiarrheal activity for the compositions of this invention was shown by a castor oil-induced diarrheal test in rats which is a modified test described by Niemegeers et al., Arzneim-Forsch 22, 516-518 (1972). The modified test was as follows. Bismuth subsalicylate (BSS) and psyllium (P) or glucomannan (GM) were evaluated alone and in ratios of 1:0.33, 1:1 and 1:3. The test materials were suspended in 0.25% methocellulose and administered to groups of 10 fasted rats via oral intubation at dosage levels ranging from 400–1,000 mg/kg. One hour following treatment, each rat was given 1.0 ml of castor oil via intubation and placed into an individual cage lined with absorbent paper. The papers were examined and replaced hourly up to 6 hours following the castor oil challenge. Antidiarrheal activity was expressed quantally as an "all-or-none response"; once an animal demonstrated evidence of diarrhea, that animal was considered to be unprotected at all subsequent time points.

The $ED_{50}$ doses were determined hourly for up to six-hours post-treatment for the individual ingredients and for the combinations. The interaction for bismuth subsalicylate and psyllium is demonstrated by data in Loewe isobolograms (S. Loewe: Pharm. Rev. 9:237–242, 1957) in the drawings. In the drawings the diagonal line joining the $ED_{50}$ values of the two drugs given separately represents simple additivity of drug effects. The dashed lines on each side of the diagonal line give the 95% confidence limits for this line of additivity. $ED_{50}$'s combinations falling under the curve (between the lower dashed line and the origin) indicate potentiation (unexpected enhancement) of effects while those above the upper dashed line would suggest antagonism between the two drugs. The 3 diagonal lines radiating from the origin represent the dose ratios of bismuth subsalicylate to psyllium used in rats receiving the combined drug dosages. The horizontal and vertical bars through each $ED_{50}$ point are the 95% confidence limits. The visual estimates from the isobolograms of the drawings indicate that in the method of the invention compositions having a ratio of bismuth subsalicylate to psyllium of from about 1:0.5 to 1:2.9 give unexpectly enhanced activity.

Likewise the data in the following table shows the percentages of rats protected over time following a single oral dose of the individual drugs as well as combination.

TABLE 1

| Material | Dose (mg/kg) | % Protected Hours Post-Challenge | | | | | |
|---|---|---|---|---|---|---|---|
| | | 1 | 2 | 3 | 4 | 5 | 6 |
| BSS | 400 | 50 | 20 | 10 | 10 | 10 | 10 |
| BSS | 800 | 80 | 40 | 30 | 30 | 30 | 30 |
| P | 400 | 70 | 10 | 0 | 0 | 0 | 0 |
| P | 800 | 60 | 20 | 10 | 10 | 0 | 0 |
| 1:1 combination | 400:400 | 90 | 80 | 60 | 60 | 60 | 60 |
| BSS | 500 | 70 | 40 | 20 | 20 | 20 | 20 |
| BSS | 1000 | 70 | 70 | 70 | 70 | 70 | 60 |
| P | 500 | 70 | 20 | 10 | 0 | 0 | 0 |
| P | 1000 | 90 | 60 | 20 | 20 | 20 | 20 |
| 1:1 combination | 500:500 | 100 | 90 | 80 | 80 | 80 | 80 |

At levels of 400 and 500 mg/kg, psyllium alone was essentially inactive and bismuth subsalicylate alone only slightly active from 3-6 hour. At levels of 800 and 1000 mg/kg, psyllium alone was only slightly active and bismuth subsalicylate at 800 mg/kg also only slightly active from 3-6 hours. Only bismuth subsalicylate at 1000 mg/kg showed a good degree of activity at 3-6 hours. In contrast, the 1:1 combinations protected 60-80% of the animals up to 6 hours. Thus, bismuth subsalicylate when combined with psyllium demonstrated much greater activity than is observed when bismuth subsalicylate is given alone and greater activity than the expected additive activity of the individual components.

The combination of BSS/GM and BSS alone produced dose-related antidiarrheal activity through six hours. However GM, when administered alone, elicited an apparent biphasic dose-response at 1 hour and was essentially inactive from 2-6 hours. Therefore, to test for interaction the activity of bismuth subsalicylate administered alone was compared with its activity when administered as a combination, under the assumption that GM did not contribute to the activity of the combination from 2 to 6 hours. $ED_{50}$'s were determined for the combination (based on its BSS content) and for BSS alone. These values, together with their relative potencies are presented below:

TABLE 2

| Post-Challenge Period* (hrs.) | $ED_{50}$ (95% C.L.) in mg/kg | | Relative Potency** |
|---|---|---|---|
| | BSS Alone | BSS Content In Combination | |
| 2 | 630 (531-748) | 473 (378-591) | 1.33 (1.01-1.75) |
| 3 | 645 (551-755) | 519 (414-652) | 1.24 (0.95-1.62) |
| 4 | 713 (601-844) | 542 (425-692) | 1.32 (1.00-1.73) |
| 5 | 763 (650-896) | 545 (434-685) | 1.40 (1.09-1.80) |
| 6 | 795 (681-929) | 532 (426-664) | 1.50 (1.16-1.92) |

*1-hour $ED_{50}$'s for BSS alone and for the BSS/GM combination were 548 (474-634) and 315 (273-365), respectively.
**Relative potency of BSS in combination with GM to BSS alone.

Thus, based on the relative potencies of the two treatments, BSS in combination with GM exhibited greater activity than expected based on its BSS content alone.

We claim:

1. An antidiarrheal composition comprising between about 100 to 3000 mg of bismuth subsalicylate and between about 50 to 9000 mg of a polymeric hydroabsorptive agent selected from the group consisting of psyllium and glucomannan wherein the weight ratio of bismuth subsalicylate to said psyllium is from about 1:0.5 to about 1:2.9 and the weight ratio of bismuth subsalicylate to said glucomannan is about 1:1.

2. A composition of claim 1 wherein the hydroabsorptive agent is psyllium.

3. A composition of claim 2 wherein the weight ratio of bismuth subsalicylate to psyllium is about 1:1.

4. A composition of claim 2 wherein the weight ratio of bismuth subsalicylate to psyllium is about 1:2.9.

5. A composition of claim 1 wherein the hydroabsorptive agent is glucommanan.

6. A composition of claim 1 wherein the weight ratio of bismuth subsalicylate to hydroabsorptive agent is about 1:1.

7. The composition of claim 1 wherein the amount of bismuth subsalicylate is between about 300 to 1000 mg and the amount of hydroabsorptive agent is between about 150 to 3000 mg and the weight ratio of bismuth subsalicylate to hydroabsorptive agent is about 1:1.

8. The composition of claim 7 wherein said hydroabsorptive agent is psyllium.

9. The composition of claim 7 wherein said hydroabsorptive agent is glycomannan.

10. The composition of claim 1 wherein the amount of bismuth subsalicylate is between about 300 to 1000 mg and the amount of psyllium is between about 150 to 3000 mg and the weight ratio of bismuth subsalicylate to psyllium is about 1:2.9.

11. A method for the remedial or preventive treatment of diarrhea symptoms comprising concurrently administering to a host in need thereof between about 100 to 3000 mg of bismuth subsalicylate and between about 50 to 9000 mg of a polymeric hydroabsorptive agent selected from the group consisting of psyllium and glucomannan wherein the weight ratio of bismuth subsalicylate to said psyllium is from about 1:05 to about 1:2.9 and the weight ratio of bismuth subsalicylate to said glucomannan is about 1:1.

12. A method of claim 11 wherein the hydroabsorptive agent is psyllium.

13. A method of claim 12 wherein the weight ratio of bismuth subsalicylate to psyllium is about 1:1.

14. A method of claim 12 wherein the weight ratio of bismuth subsalicylate to psyllium is about 1:2.9.

15. A method of claim 11 wherein the hydroabsorptive agent is glucomannan.

16. A method of claim 11 wherein the weight ratio of bismuth subsalicylate to hydroabsorptive agent is about 1:1.

17. The method of claim 11 wherein the amount of bismuth subsalicylate is between about 300 to 1000 mg and the amount of psyllium is between about 150 to 3000 mg and the weight ratio of bismuth subsalicylate to psyllium is about 1:2.9.

18. A method for the remedial or preventive treatment of diarrhea symptoms comprising concurrently administering to a host in need thereof between about 300 to 1000 mg of bismuth subsalicylate and between about 150 to 3000 mg of a polymeric hydroabsorptive agent selected from the group consisting of psyllium and glucomannan wherein the weight ratio of bismuth subsalicylate to said psyllium is from about 1:0.5 to about 1:2.9 and the weight ratio of bismuth subsalicylate to said glucomannan is about 1:1.

19. The method of claim 18 wherein said hydroabsorptive agent is psyllium.

20. The method of claim 18 wherein said hydroabsorptive agent is glycomannan.

* * * * *